United States Patent [19]

Mutsukado et al.

[11] 4,412,082

[45] Oct. 25, 1983

[54] METHOD FOR PREPARING 4-HYDROXYPHENYLACETIC ACID

[75] Inventors: Motoo Mutsukado; Shin Yamada, both of Funabashi, Japan

[73] Assignee: Nissan Chemical Industries, Ltd., Tokyo, Japan

[21] Appl. No.: 353,948

[22] Filed: Mar. 2, 1982

[30] Foreign Application Priority Data

Mar. 13, 1981 [JP] Japan .................................. 56-36327

[51] Int. Cl.$^3$ ............................................. C07C 65/01
[52] U.S. Cl. .................... 562/478; 568/630; 568/631; 568/647; 568/655; 260/465 F
[58] Field of Search ......................................... 562/478

[56] References Cited

U.S. PATENT DOCUMENTS 4,178,460  12/1979  Berkelhammer et al. .......... 562/478

*Primary Examiner*—Paul J. Killos
*Attorney, Agent, or Firm*—Frishauf, Holtz, Goodman & Woodward

[57] ABSTRACT

A novel process for preparing 4-hydroxyphenylacetic acid which is useful as an intermediate for pharmaceutical is provided. A method for preparing 4-hydroxyphenylacetic acid comprising the steps of first reacting benzyl phenyl ether with formaldehyde and hydrogen chloride to form 4-benzyloxybenzyl chloride, second reacting the resultant 4-benzyloxybenzyl chloride with an alkali metal cyanide in at least one solvent selected from the group consisting of water and an organic solvent to form 4-benzyloxyphenylacetonitrile, and hydrolyzing the resultant 4-benzyloxyphenylacetonitrile in the presence of an acid catalyst.

13 Claims, No Drawings

METHOD FOR PREPARING 4-HYDROXYPHENYLACETIC ACID

The present invention relates to an industrially advantageous method for preparing 4-hydroxyphenylacetic acid represented by the following formula (I):

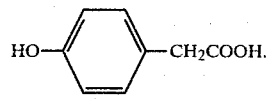
(I)

4-Hydroxyphenylacetic acid is an important intermediate which is used for syntheses of substances useful for pharmaceuticals. Therefore, it is generally beneficial that the acid is advantageously manufactured on an industrial scale.

As typical examples for the synthesis of 4-hydroxyphenylacetic acid, there have heretofore been known the following methods:

(1) A method in which anisole, which is a starting material, is subjected to chloromethylation and a cyanation to be thereby converted to 4-methoxyphenylacetonitrile (Organikum, Berlin, nine edit., p. 363); and the resultant 4-methoxyphenylacetonitrile is saponified to produce an acid, which is subsequently treated with hydriodic acid to eliminate an ether, whereby 4-hydroxyphenylacetic acid is obtained as the desired product (J. Org. Chem., Vol. 22, 1957, p. 1577).

(2) A method in which the starting material, p-cresol, is acetylated to form 4-acetoxytoluene, which is subsequently brominated to obtain 4-acetoxybenzyl bromide, followed by cyanation to be converted to 4-hydroxyphenylacetonitrile.

(3) A method in which phenol, which is a starting material, is subjected to the Friendel-Crafts reaction to produce 4-hydroxyacetophenone, and then to the Willgerodt-Kindler reaction to obtain 4-hydroxyphenylacetic acid.

(4) A method in which the starting material, phenol (or o-chlorophenol) is allowed to react with glyoxylic acid to obtain 4-hydroxymandelic acid (or 3-chloro-4-hydroxymandelic acid), followed by catalytic hydrogenenation to produce 4-hydroxyphenylacetic acid (Japanese Provisional Patent Publications Nos. 125635/1979 and corresponding U.S. Pat. No. 4,329,497 and 148745/1979 and corresponding U.S. Pat. No. 4,198,523.)

These methods, however, have some disadvantages such as low yield, poor crystallizability of the intermediates so that they have extreme difficulties in separation and purification thereof, and requires employment of expensive materials. Therefore any of the methods mentioned above is hardly considered to be a satisfactory industrial method of manufacturing the desired product. For example, in the case of the method in item (1) above, the crystallizability of 4-methoxybenzyl chloride is poor, which fact renders difficult the separation and purification of 2-methoxybenzyl chloride and thus exerts a bad influence upon the purity of the final product. Further, in view of the fact that expensive agents such as hydroiodic acid must be used for the cleavage of the methyl group, the method (1) can scarcely be considered to be industrially advantageous.

Also in the case of the method in item (2) mentioned above, the acetoxy group is easily hydrolyzed under alkaline conditions, so that at least 2 equivalents of the cyanating agent is necessary. Thus, the operation involves danger and the crystallizability of 4-hydroxyphenylacetonitrile which is the desired product is poor, which makes its purification difficult. In consequence, the method in item (2) is not always industrially advantageous.

Also in the case of the method in item (3) above, the total yield is as less as 30%, and the method causes waste water problems with sulfides which are produced as by-products. Therefore, this method also has problems when applied industrially.

As for the method in item (4) above, although the starting material itself is inexpensive, the process has operational problems in that the isolation of 4-hydroxy mandelic acid which is an intermediate requires a large quantity of a solvent for extraction. In view of such problems, the method in (4) is not always an advantageous industrial manufacturing process.

Therefore, it has been a task in the art to provide a method for preparing 4-hydroxyphenylacetic acid in good yield without any drawbacks just described.

The present inventors have intensively researched taking such circumstances into account with the intention of seeking for some industrial method by which the desired product can easily be produced economically, and as a result they have found out an excellent industrial method capable of solving the above-mentioned problems and have completed the present invention.

The method of the present invention will be illustrated as follows:

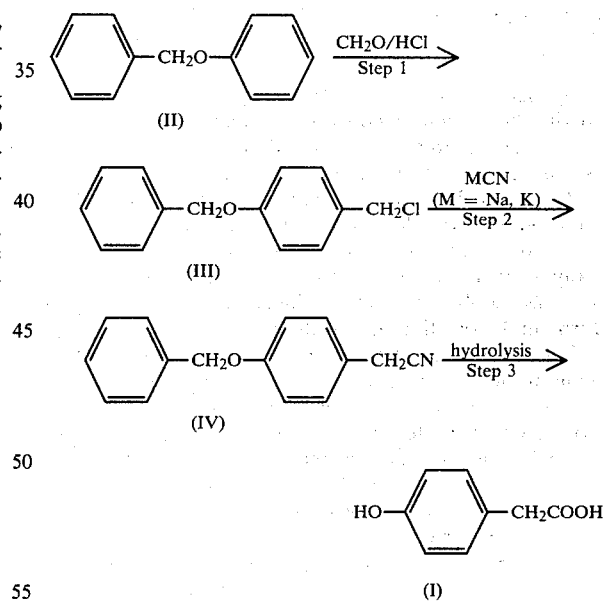

Each process of the method will be explained below:

Step 1

In this first process, the benzyl phenyl ether represented by the above formula (II) is reacted with formaldehyde and hydrogen chloride to prepare 4-benzyloxybenzyl chloride represented by the above formula (III).

Conventional examples of methods for preparing 4-benzyloxybenzyl chloride represented by the above formula (III) are disclosed in U.S. Pat. No. 2,571,954 and on pages 5491 to 5495, Vol. 75 of J. Am. Chem. Soc. According to these known methods, however, 4-benzyloxybenzaldehyde is changed into the corresponding alcohol, and hydrogen chloride is utilized to convert the alcohol to the chloride, therefore they comprises many steps and thus are not always considered to be convenient industrial processes. The method of the present invention has been developed to overcome these disadvantages. Benzyl phenyl ether which is a starting material in this step can almost quantitatively and inexpensively be obtained by reacting phenol and benzyl chloride in the presence of a base.

This step is intended to introduce a chloro methyl group into the 4-position of benzyl phenyl ether which is the starting material, by reacting the ether with formaldehyde and hydrogen chloride. As the formaldehyde to be used, there may be employed a commercially available 40% aqueous solution thereof or paraformaldehyde. Futher, as the hydrogen chloride, hydrogen chloride gas is especially preferred but a concentrated hydrochloric acid may also be usable. If desired, a hydrogen chloride gas may be blown into a concentrated hydrochloric acid to obtain a good result.

The reaction proceeds sufficiently even in a solventless state, but a more preferably result can be obtained when a solvent inert to the reaction such as an organic acid, e.g. acetic acid, benzene, toluene or the like is added. The reaction may be carried out over a wide temperature range of 0° to 120° C. At such a temperature, the reaction can be completed enough in one to 15 hours. After completion of the reaction, water and an organic solvent are added to the reaction mixture, and the resultant organic layer is dried and concentrated, followed by crystallization or vacuum distilation to easily obtain the desired product.

Step 2

In this step, 4-benzyloxybenzyl chloride represented by the above-mentioned formula (III) is reacted with an alkali metal cyanide in water and/or an organic solvent to prepare 4-benzyloxyphenylacetonitrile.

As the alkali metal cyanide which can be used in this step sodium cyanide or potassium cyanide is preferred.

As the solvent to be used, there may be used an organic solvent which does not participate in the reaction, such as alcohol, benzene, toluene, exylene, dimethylformamide or dimethyl sulfoxide, as well as water. When water and a water-insoluble solvent such as benzene, toluene or xylene is used as the solvent, a minor amount of a quaternary ammonium salt may be added to obtain a more preferable result. A temperature of 10° C. to 150° C. is applicable in the reaction, but a preferred temperature is between 20° C. to 120° C. After completion of the reaction, an organic solvent such as toluene, which is water-insoluble, and water are added to the reaction mixture and the resultant organic layer is dried and concentrated, followed by crystallization or vacuum distilation to easily isolate the desired product.

Step 3

In this step, the benzyloxyphenylacetonitrile represented by the above-mentioned formula (IV) is hydrolyzed in the presence of an ordinary acid catalyst to prepare 4-hydroxyphenylacetic acid represented by the aforesaid formula (I).

As the acid catalyst, an ordinary inorganic acid such as hydrogen chloride, hydrochloric acid or sulfuric acid can be employed. In this case, especially when hydrogen chloride and/or hydrochloric acid is used, benzyl chloride is yielded almost quantitatively as a by-product together with the desired product. Benzyl chloride is reusalbe in the step in which benzyl phenyl ether, a starting material in the first step, is manufactured, therefore it is possible to design an industrially rational steps of procedure.

As mentioned above, the present invention is characterized by making use of a benzyl group as a protective group in each process, and this attempt is quite novel in the field of the method of manufacturing 4-hydroxyphenylacetic acid. In the present invention, the benzyl group introduced, whereby the crystallizability of the intermediates in each step becomes good and therefore the separation and purification becomes also extremely easy. Further, materials themselves to be used are inexpensive, additionally a yield in each step is noticeably good, and manufacturing operation is simple. In view of the fact, the preparation method of the present invention can be considered to be industrially excellent.

Now, the present invention will illustratively be explained with reference to the following Examples.

EXAMPLE 1

Preparation of 4-benzyloxybenzyl chloride (Step 1)

In a 1 l four-necked flask, there were placed 85.4 g (0.464 mole) of benzyl phenyl ether, 45 g (1.5 moles) of paraformaldehyde, 300 ml of conc. hydrochloric acid and 100 ml of benzene, and the resulting mixture was stirred for 4 hours at 50° to 60° C. After completion of the reaction, 100 ml of toluene was added to the resulting reaction mixture followed by vigorous stirring of the resulting mixture. The resulting organic layer in the mixture was washed twice with 200 ml of water. The thus obtained organic layer was dried over anhydrous sodium sulfate followed by removal of the solvent by evaporation. To the so obtained viscous oily substance were added about 200 ml of n-heptane and 50 ml of ethyl ether. Upon stirring of the resulting mixture at room temperature, crystals precipitated. After allowing the mixture to stand overnight, the crystals were collected by filtration and dried to give 30.5 of 4-benzyloxybenzyl chloride.

Melting point: 78°–80° C. [recrystallized from n-heptane, lit. (according to literature) 79°–80° C.]

NMR (CDCl$_3$), δppm: 4.45 (s, 2H), 4.95 (s, 2H), 6.86 (d, 2H), 7.23 (s, 2H).

EXAMPLE 2

Preparation of 4-benzyloxybenzyl chloride (Step 1)

In a 1 l four-necked flask, there were placed 73.6 g (0.4 mole) of benzyl phenyl ether, 24 g (0.8 mole) of paraformaldehyde and 50 ml of benzene. To the resulting mixture was introduced hydrogen chloride at a rate of 66 ml/minute under stirring to effect the reaction for 8 hours.

After completion of the reaction, 45 g of benzene and 100 g of water were added to the resulting reaction mixture, and the obtained organic layer was washed with water. Analysis of the organic layer by way of high-speed liquid chromatography revealed that 65.1 g (0.28 mole) of 4-benzyloxybenzyl chloride was contained therein.

The organic layer was evaporated to distil out 50 g of benzene and the residue was allowed to stand at room temperature to precipitate crystals. The thus precipitated crystals were collected by filtration and dried to give 50 g (purity: 95%) of 4-benzyloxybenzyl chloride as white crystals.

EXAMPLE 3

Preparation of 4-benzyloxyphenylacetonitrile (Step 2)

In 50 ml of dimethylformamide was dissolved 5.0 g (0.02 mole) of 4-benzyloxybenzyl chloride, and 1.7 g (0.026 mole) of potassium cyanide was added to the resulting solution followed by stirring at 40° to 50° C. for about 3 hours.

After completion of the reaction, 50 ml of toluene and 50 ml of water were added to the resulting reaction mixture followed by vigorous stirring. The obtained organic layer was washed twice with 50 ml of water. After the organic layer was dried over anhydrous sodium sulfate, the solvent was removed by distillation and the residue was dried to give 4.45 g of crystals.

Melting point: 69–69.5 [recrystallized from a mixed solvent of benzene and heptane (1:1), lit. (Chemical Abstract, 46, 5062a) 68.5°–69° C.].

NMR (CDCl$_3$), δppm: 3.54 (s, 2H), 4.98 (s, 2H), 6.86 (d, 2H), 7.19 (d, 2H).

EXAMPLE 4

Preparation of 4-benzyloxyphenylacetonitrile (Step 2)

In a 100 ml four-necked flask, there were placed 3.2 g of water, 1.23 g (0.025 mole) of sodium cyanide and 0.16 g of triethylbenzylammonium chloride, and a solution prepared by dissolving 5.3 g (0.023 mole) of 4-benzyloxybenzyl chloride in 6 g of benzene was further added thereto under stirring. Then, the resultant mixture was heated at a temperature of 80° C. for 5 hours under stirring to permit a reaction. After completion of the reaction, the formed organic layer is washed with water and dried over anhydrous sodium sulfate, followed by distilling off benzene to obtain 4.83 g (0.022 mole) of 4-benzyloxyphenylacetonitrile.

EXAMPLE 5

Preparation of 4-hydroxyphenylacetic acid (Step 3)

In 20 ml of ethanol was dissolved 2.0 g (0.009 mole) of 4-benzyloxyphenylacetonitrile to give a solution. After addition of 25 ml of conc. hydrochloric acid thereto, the mixture was heated at 100° C. under stirring for 3 hours.

After completion of the reaction, the solvent was removed by distillation. After 50 ml of a 10% aqueous caustic soda (sodium hydroxide) was added to the residue and the mixture was stirred, 30 ml of toluene was added thereto followed by vigorous shaking. The aqueous layer thus obtained was adjusted to pH 2-3 by using an aqueous hydrochloric acid followed by extraction with 50 ml of ethyl acetate. After the thus obtained organic layer was dried over anhydrous sodium sulfate and the solvent was removed by evaporation, 1.1 g (0.007 mole) of the desired product was obtained as white crystals.

Melting point: 149°–151° C.

NMR (DMSO-d$_6$+CDCl$_3$), δppm: 3.48 (s, 2H), 6.75 (d, 2H), 7.10 (d, 2H).

EXAMPLE 6

Preparation of 4-hydroxyphenylacetic acid (Step 3)

After 4.46 g (0.02 mole) of 4-benzyloxyphenylacetonitrile was dissolved in a mixture of 10 ml of toluene and 2 g of dimethylformamide, 3.32 g of conc. hydrochloric acid was added thereto. The resulting mixture was stirred under heating for 5 hours with introduction thereto of hydrogen chloride gas at a rate of 6 ml/minute to effect the reaction.

After completion of the reaction, the solvent was removed by evaporation. After ethyl acetate and water were added to the resulting residue, the mixture was stirred. The thus obtained organic layer was dried over anhydrous sodium sulfate. Gas-chromatographic analysis of the organic layer revealed that 2.74 g (0.018 mole) of 4-hydroxyphenylacetic acid was contained therein.

We claim:

1. A method for preparing 4-hydroxyphenylacetic acid comprising the steps of first reacting benzyl phenyl ether with formaldehyde and hydrogen chloride to form 4-benzyloxybenzyl chloride, second reacting the resultant 4-benzyloxybenzyl chloride with an alkali metal cyanide in at least one solvent selected from the group consisting of water and an organic solvent to form 4-benzyloxyphenylacetonitrile, and hydrolyzing the resultant 4-benzyloxyphenylacetonitrile in the presence of an acid catalyst.

2. The method for preparing 4-hydroxyphenylacetic acid according to claim 1, wherein said formaldehyde is a 40% aqueous solution thereof or paraformaldehyde.

3. The method for preparing 4-hydroxyphenylacetic acid accordiing to claim 1, wherein said hydrogen chloride is hydrogen chloride gas or a concentrated hydrochloric acid.

4. The method for preparing 4-hydroxyphenylacetic acid according to claim 1, wherein said hydrogen chloride is the gas which is blown into a concentrated hydrochloric acid.

5. The method for preparing 4-hydroxyphenylacetic acid according to claim 1, wherein said first reaction is carried out in a solvent of acetic acid, benzene or toluene.

6. The method for preparing 4-hydroxyphenylacetic acid according to claim 1, wherein said first reaction is carried out at a temperature of 0° to 120° C. for one to 15 hours.

7. The method for preparing 4-hydroxyphenylacetic acid according to claim 1, wherein said alkali metal cyanide is sodium cyanide or potassium cyanide.

8. The method for preparing 4-hydroxyphenylacetic acid according to claim 1, wherein said organic solvent is alcohol, benzene, toluene, xylene, dimethylformamide or dimethylsulfoxide.

9. The method for preparing 4-hydroxyphenylacetic acid according to claim 1, wherein when water and a water-insoluble solvent are used as said solvent, a quaternary ammonium salt is further added.

10. The method for preparing 4-hydroxyphenylacetic acid according to claim 1, wherein said second reaction between 4-benzyloxybenzyl chloride and an alkali metal cyanide is carried out at a temperature of 10° to 150° C.

11. The method for preparing 4-hydroxyphenylacetic acid according to claim 10, wherein said second reaction is carried out at a temperature of 20° to 120° C.

12. The method for preparing 4-hydroxyphenylacetic acid according to claim 1, wherein said acid catalyst is at least one acid selected from the group consisting of hydrogen chloride, hydrochloric acid and sulfuric acid.

13. The method for preparing 4-hydroxyphenylacetic acid according to claim 1, wherein in said first step, said formaldehyde is a 40% aqueous solution thereof or paraformaldehyde and said first step is carried out at a temperature of 0° to 120° C. for 1 to 15 hours in a solvent of acetic acid, benzene or toluene; in said second step, said alkali metal cyanide is sodium cyanide or potassium cyanide, said organic solvent is alcohol, benzene, toluene, xylene, dimethylformamide or dimethylsulfoxide and said second reaction is carried out at a temperature of 20° to 120° C.; and said acid catalyst is at least one acid selected from the group consisting of hydrogen chloride, hydrochloric acid and sulfuric acid.

* * * * *